United States Patent
Yoshiba

(10) Patent No.: US 10,376,425 B2
(45) Date of Patent: Aug. 13, 2019

(54) ABSORBENT ARTICLE

(71) Applicant: Daio Paper Corporation, Shikokuchuo-shi, Ehime (JP)

(72) Inventor: Megumi Yoshiba, Sakura (JP)

(73) Assignee: Daio Paper Corporation, Ehime (JP)

( * ) Notice: Subject to any disclaimer, the term of this patent is extended or adjusted under 35 U.S.C. 154(b) by 744 days.

(21) Appl. No.: 14/764,789

(22) PCT Filed: Dec. 27, 2013

(86) PCT No.: PCT/JP2013/085120
§ 371 (c)(1),
(2) Date: Jul. 30, 2015

(87) PCT Pub. No.: WO2014/119218
PCT Pub. Date: Aug. 7, 2014

(65) Prior Publication Data
US 2015/0366722 A1    Dec. 24, 2015

(30) Foreign Application Priority Data

Jan. 31, 2013 (JP) .................. 2013-016659

(51) Int. Cl.
| | |
|---|---|
| *A61F 13/15* | (2006.01) |
| *A61F 13/475* | (2006.01) |
| *A61F 13/515* | (2006.01) |
| *A61F 13/539* | (2006.01) |
| *A61F 13/47* | (2006.01) |

(Continued)

(52) U.S. Cl.
CPC ........ *A61F 13/4756* (2013.01); *A61F 13/515* (2013.01); *A61F 13/539* (2013.01); *A61F 2013/15365* (2013.01)

(58) Field of Classification Search
CPC .......... A61F 13/15; A61F 13/47; A61F 13/53; A61F 13/51
See application file for complete search history.

(56) References Cited

U.S. PATENT DOCUMENTS

| | | | | |
|---|---|---|---|---|
| 4,886,697 A | * | 12/1989 | Perdelwitz, Jr. | ..... A47C 27/005 428/192 |
| 2015/0133882 A1 | * | 5/2015 | Becker | .............. A61F 13/15203 604/366 |

FOREIGN PATENT DOCUMENTS

| | | |
|---|---|---|
| JP | 5-39691 | 10/1993 |
| JP | 2007-89818 | 4/2007 |

(Continued)

*Primary Examiner* — Tatyana Zalukaeva
*Assistant Examiner* — Ilya Y Treyger
(74) *Attorney, Agent, or Firm* — Norris McLaughlin, P.A.

(57) ABSTRACT

On a wearer's body contact surface of a sanitary napkin, an emboss is provided in such a pattern that a plurality of straight portions and arc-shaped portions which protrude outwardly in the direction of the width of the napkin, with the ends of the straight portions being base points, are alternately arranged. A plurality of arc-shaped portions are arranged, and thus the resistance to a leg pressure from the outside in the width direction is increased, with the result that the absorber is unlikely to be wrinkled and leakage caused by the wrinkle is unlikely to occur. The flow of a body fluid diffused from the center in the width direction toward the outside in the longitudinal direction of the napkin along the straight portion is produced, and thus the diffusion in the width direction is reduced, with the result that side leakage is unlikely to occur.

7 Claims, 9 Drawing Sheets

(51) Int. Cl.
  *A61F 13/53* (2006.01)
  *A61F 13/51* (2006.01)
  *C08L 77/00* (2006.01)
  *A01K 23/00* (2006.01)
  *A47L 13/17* (2006.01)

(56) References Cited

FOREIGN PATENT DOCUMENTS

| JP | 2009-125485 | 6/2009 |
| JP | 2010-136972 | 6/2010 |
| JP | 2012-70974 | 4/2012 |

* cited by examiner

Fig. 8
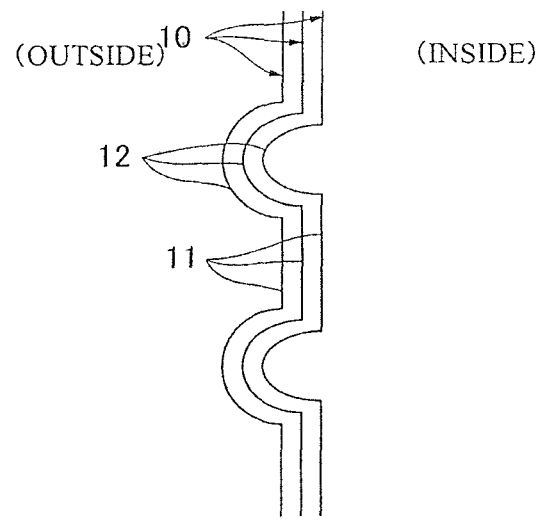
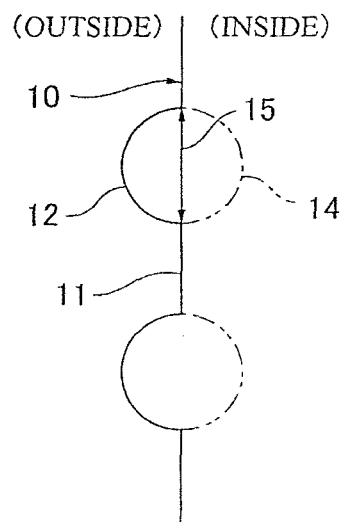
Fig. 9(A)
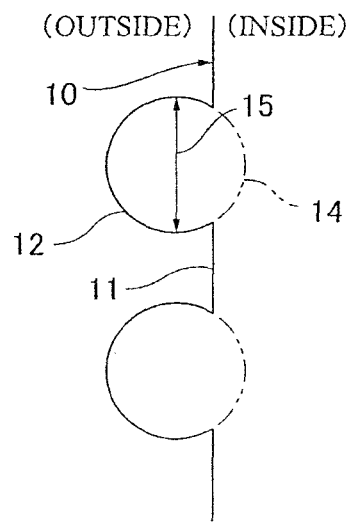
Fig. 9(B)
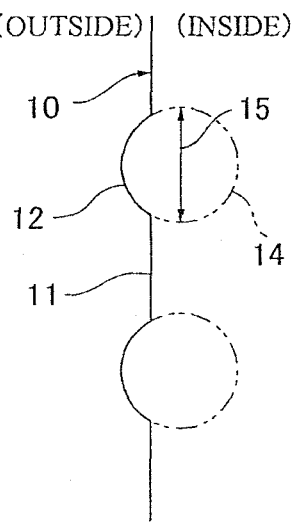
Fig. 9(C)

ABSORBENT ARTICLE

BACKGROUND OF THE INVENTION

The present invention mainly relates to absorbent articles used in a sanitary napkin, a parity liner, an incontinence pad, a medical pad and a personal hygiene item, and particularly relates to absorbent articles in which, even when an absorber is relatively thin, the absorber is unlikely to be wrinkled, and side leakage is unlikely to occur.

Conventionally, as the absorbent article, an absorbent article is known in which an absorber formed of cellulose wadding (where high water-absorbent resin is mixed) such as pulverized pulp is interposed between a liquid-impermeable back sheet such as a polyethylene sheet or a polyethylene sheet laminate non-woven fabric and a liquid-permeable surface sheet such as a non-woven fabric or a liquid-permeable plastic sheet.

In recent years, disadvantageously, in the case of a relatively bulky absorbent article, for example, it has been inconvenient to carry it around or it has been difficult to store, and since making physical distribution more efficient, resource saving and the like are required, a thin absorbent article in which the thickness of an absorber in a body fluid discharge site is 8 mm or less and is preferably 5 mm or less tends to be desired.

However, it is conventionally known that disadvantageously when the thickness of an absorber is reduced, the absorber is wrinkled due to leg pressure and the like, and thus side leakage is more likely to occur. As a technology for preventing such a wrinkle or the like, Japanese Unexamined Patent Application Publication No. 2009-125485 that will be described below discloses an absorbent article in which in at least an excretory part opposite portion of an absorbent main body, a pair of side portions of an absorber are compressed more than a width direction center portion located between the pair of side portions, and thus a pair of highly compressed areas are formed and the highly compressed areas are formed up to a width direction outer end portion of the absorber and are not formed up to longitudinal direction front/back end portions of the absorber.

Japanese Unexamined Patent Application Publication No. 2010-136972 that will be described below discloses an absorbent article in which in both side portions of a surface sheet and an absorber in an excretory part region, a pair of inside grooves curved in a convex shape outwardly in a width direction in plan view are formed, and in the surface sheet and the absorber outside in the width direction in each of the pair of inside grooves, a pair of outside grooves curved in a convex shape outwardly in the width direction in plan view are formed.

SUMMARY OF THE INVENTION

However, in the absorbent article disclosed in Japanese Unexamined Patent Application Publication No. 2009-125485 described above, since the highly compressed areas are formed only in both side portions of a body fluid discharge portion of the absorber, and the highly compressed areas are not formed up to the front/back end portion, the effect of diffusing the absorbed body fluid back and forth is reduced, and thus there is a large danger that the body fluid is more likely to be stored in the vicinity of the body fluid discharge portion and that side leakage occurs. In the front/back portions where the absorber is not compressed, the absorber is more likely to be wrinkled, and this wrinkle causes the adhesion to skin to be lowered, with the result that leakage is more likely to occur.

In the absorbent article disclosed in Japanese Unexamined Patent Application Publication No. 2010-136972 described above, the pair of inside grooves and the pair of outside grooves are formed so as to compact the absorber, and thus a wrinkle is unlikely to be produced. However, since the inside grooves and the outside grooves are simply curved in a convex shape outwardly in the width direction, it is difficult to obtain a sufficient resistance to the leg pressure from the outside in the width direction, with the result that there is a possibility that the absorber is wrinkled.

Hence, a main object of the present invention is to provide an absorbent article in which an absorber is unlikely to be wrinkled and in which side leakage is unlikely to occur.

To achieve the object according to the present invention, there is provided an absorbent article in which an absorber is interposed between a liquid-permeable surface sheet and a back sheet and an emboss is provided in each of the both side portions of the absorber along a substantially longitudinal direction, where the emboss is formed in such a pattern that a plurality of alternately arranged straight portions and arc-shaped portions which protrude outwardly in a direction of a width of the absorbent article with the ends of the straight portions being base points for the arc-shaped portions.

In a first aspect of the present invention, since the emboss that is provided in each of the both side portions of the absorber along a substantially longitudinal direction is formed in such a pattern that the plurality of straight portions and arc-shaped portions which protrude outwardly in the direction of the width of the absorbent article with the ends of the straight portions being the base points for the arc-shaped portions are alternately arranged, the rigidity of both side portions of the absorber is enhanced, and the resistance to leg pressure is enhanced, with the result that the absorber is unlikely to be wrinkled and that leakage caused by the wrinkle can be prevented. In particular, since the emboss includes a plurality of arc-shaped portions which protrude outwardly in the width direction with the ends of the straight portions being the base points for the arc-shaped portions, leg pressure from the outside in the width direction is dispersed and absorbed by the arc-shaped portions and is securely received by the arc-shaped portions, with the result that it is possible to reliably prevent the absorber from being wrinkled.

Since the straight portions are provided between the arc-shaped portions, when the body fund diffused from the center side in the width direction toward the outside reaches a straight portion, the flow is converted into the flow in the direction along the straight portion, that is, the flow in the direction along a substantially longitudinal direction of the absorbent article, and thus the diffusion toward the outside in the width direction is reduced, with the result that it is possible to reliably prevent side leakage.

According to a second aspect of the present invention, the absorbent article of the first aspect is provided where, hi the emboss, the base point to base point linear dimension of the arc-shaped portion in a longitudinal direction of the absorbent article is formed to be longer than the straight portion in the longitudinal direction of the absorbent article.

In the second aspect of invention, the dimensions of the individual portions of the emboss in the longitudinal direction of the absorbent article are specified, and the length of the arc-shaped portion is made longer than that of the straight portion, and thus the resistance to leg pressure is enhanced, with the result that the absorber is prevented from being wrinkled.

According to a third aspect of the present invention, the absorbent article, of the first or second aspect is provided where a plurality of the embosses are formed in each of both the side portions of the absorber, and in the embosses located outwardly in the width direction, as compared with the embosses located inwardly in the width direction, a distance between the adjacent embosses is narrower and/or a width of a groove of the emboss is greater.

In the third aspect of the invention, when a plurality of the embosses are formed in each of both the side portions of the absorber, in the embosses located outwardly in the width direction, as compared with the embosses located inwardly in the width direction, the distance between the adjacent embosses is narrower and/or the width of the groove of the emboss is greater. In this way, on the outside in the width direction, as compared with the inside in the width direction, the rigidity of the absorber is enhanced, the absorber can be prevented from being wrinkled and the direction of the diffusion of the body fluid is easily converted into the direction along the straight portion.

According to a fourth aspect of the present invention, the absorbent article of any of the first to third aspects of the invention is provided where in the emboss, the width of the groove of the arc-shaped portion is greater than the width of a groove of the straight portion.

In the fourth aspect of the invention, in the arc-shaped portion that mainly plays a role in resisting the leg pressure from the outside in the width direction, the width of the groove of the arc-shaped portion is set greater than the width of the groove of the straight portion, and thus the resistance to the leg pressure is further enhanced, with the result that the absorber is prevented from being wrinkled.

According to a fifth aspect of the present invention, the absorbent article of any of the first to fourth aspects of the invention is provided where a plurality of the embosses are formed in each of both side portions of the absorber, and under conditions in which the adjacent embosses are arranged a distance apart so as not to intersect each other, part of the arc-shaped portion of the emboss located inwardly in the width direction is arranged so as to enter an inside of the arc-shaped portion of the emboss located outwardly in the width direction.

In the fifth aspect of invention, when a plurality of embosses are formed in both side portions of the absorber, part of the arc-shaped portion of the emboss located on the inside in the width direction is arranged to enter the inside of the arc-shaped portion located on the outside in the width direction such that the embosses are provided in the shape of multiple lines. In this way, it is possible to further enhance the rigidity of the arc-shaped portion, thereby increasing resistance to the leg pressure and further preventing the absorber from being wrinkled.

According to a sixth aspect of the present invention, the absorbent article of any of first to fifth aspects is provided where a section corresponding to a groin portion when worn has any one of a configuration in which, as compared with sections in a front and back thereof, the width of the groove of the arc-shaped portion is greater; a configuration in which the linear dimension of the arc-shaped portion in the longitudinal direction of the absorbent article is longer; a configuration in which the dimension of the straight portion in the longitudinal direction of the absorbent article is shorter; a configuration in which a radius of curvature of the arc-shaped portion is smaller; and a configuration in which an amount of protrusion of the arc-shaped portion outwardly in the direction of the width of the absorbent article with the ends of the straight portions being the base points is greater, or has an arbitrary combination thereof.

In the sixth aspect of the invention, since the section corresponding to the groin portion when the absorbent article is worn is a portion on which the leg pressure particularly significantly acts, as a means that increases the resistance to the leg pressure to prevent wrinkling, some configurations for enhancing the rigidity of the absorber are specified.

According to a seventh aspect of the present invention, the absorbent article of any of the first to sixth aspects is provided where a coupling portion that connects ends of the straight portions with a linear emboss is formed such that the straight portions and the coupling portions form one continuous line.

In the seventh aspect of the invention, the coupling portion that connects the ends of the straight portions with the linear emboss is formed such that the straight portions and the coupling portions form one continuous line, with the result that the body fluid is easily diffused in the longitudinal direction.

According to an eighth aspect of the present invention, the absorbent article of any of the first to seventh aspects is provided where the embosses are formed along a longitudinal direction of the absorbent article either continuously or intermittently. The present invention specifies that the embosses can be formed along a longitudinal direction of the absorbent article not only continuously but also intermittently.

According to a ninth aspect of the present invention, the absorbent article of any of the first to fourth and sixth to eighth aspects of the invention is provided where a plurality of the embosses are formed in each of both side portions of the absorber, and the arc-shaped portions of the adjacent embosses in a widthwise direction of the absorbent article are out of phase.

In the ninth aspect of the invention, the arc-shaped portions of the adjacent embosses in a widthwise direction of the absorbent article are out of phase. In this way, since the arc-shaped portions are present over a wider range in the longitudinal direction of the absorbent article, leg pressure is reliably resisted.

As described in detail above, in the present invention, it is possible to provide an absorbent article in which an absorber is unlikely to be wrinkled and in which side leakage is unlikely to occur.

BRIEF DESCRIPTION OF THE DRAWINGS

FIG. 8 is an enlarged view (No. 4) of the emboss 10;

FIGS. 9(A), 9(B) and 9(C) are enlarged views (No. 5) of the emboss 10;

DETAILED DESCRIPTION OF THE INVENTION

Embodiments of the present invention will be described in detail below with reference to drawings.

[Basic Configuration of Sanitary Napkin 1]

Figure 1:
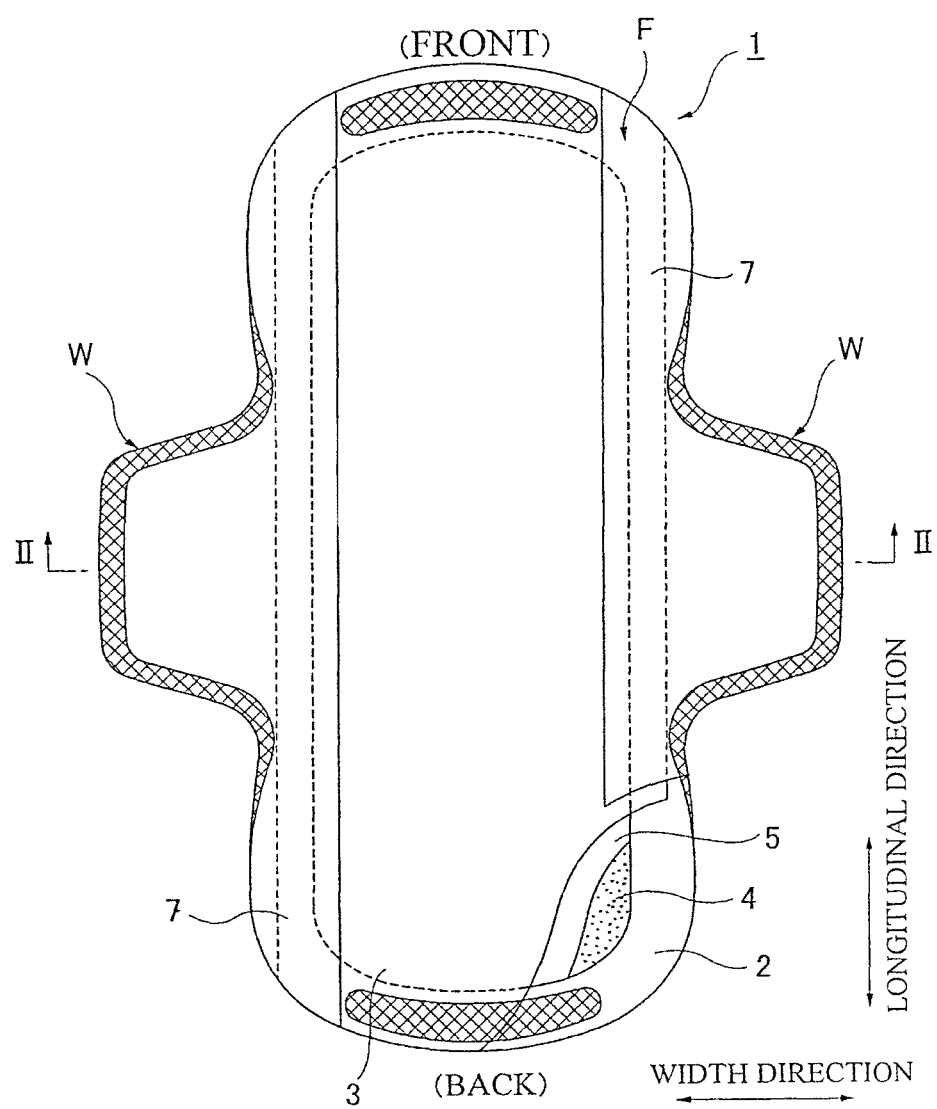
FIG. 1 is a partially broken development view of a sanitary napkin 1 according to the present invention.
Figure 2:
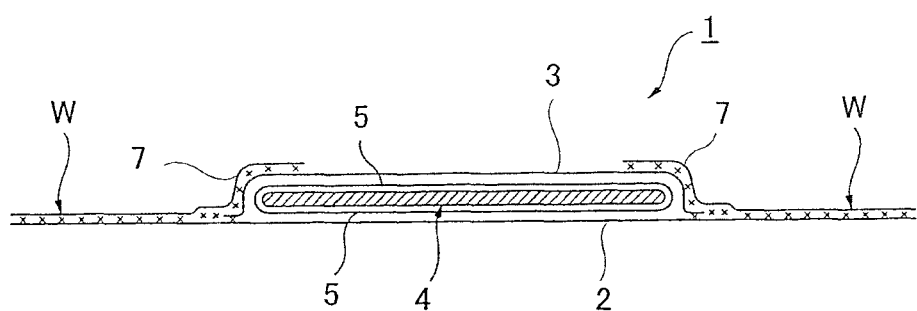
FIG. 2 is a cross-sectional view taken along line II-II of FIG. 1.

As shown in FIG. 1, a sanitary napkin 1 according to the present invention is formed with a liquid-impermeable back sheet 2 formed with a polyethylene sheet or a polypropylene sheet; a liquid-permeable surface sheet 3 that rapidly transmits menstrual blood and vaginal discharge; an absorber 4 that is interposed between these sheets 2 and 3 and that is formed of cotton-like pulp, synthetic pulp or the like; crepe paper 5 that wraps the absorber 4 to hold the shape of the absorber 4 and enhance the diffusivity; and side non-woven fabrics 7 that are provided at both side portions along the longitudinal direction. In the surrounding area of the absorber 4, in the front/back end edge portions in the longitudinal direction of the napkin, the outer edge portions of the liquid-impermeable back sheet 2 and the liquid-permeable surface sheet 3 are joined with an adhesive such as a hot melt or an adhesive means such as a heat seal, and in the both side edge portions, the liquid-impermeable back sheet 2 and the side non-woven fabrics 7 extending out laterally as compared with the end edges of the absorber 4 are joined with an adhesive such as a hot melt or an adhesive means such as a heat seal, with the result that a peripheral flap portion F where the absorber 4 is not present in the periphery is formed.

The structure of the sanitary napkin 1 will be described in further detail below. As the liquid-impermeable back sheet 2, a sheet material, such as an olefin resin sheet such as polyethylene or polypropylene, that provides at least aqueous shielding is used. Alternatively, a laminate non-woven fabric obtained by stacking a non-woven fabric on a polyethylene sheet or the like in layers, or a non-woven fabric sheet in which a waterproof film is interposed to practically acquire liquid imperviousness (in this case, the waterproof film and the non-woven fabric constitute the liquid-impermeable back sheet) or the like can be used. In recent years, in terms of sweat prevention, a sheet having moisture permeability has tended to be used. The aqueous shielding and moisture-permeable sheet material described above is a microporous sheet obtained by melting and kneading an inorganic filler into an olefin resin such as polyethylene or polypropylene to form a sheet and thereafter stretching the sheet in a uniaxial or biaxial direction.

Next, as the liquid-permeable surface sheet 3, a porous or non-porous non-woven fabric, a porous plastic sheet or the like is preferably used. As the material fiber of the non-woven fabric, for example, a synthetic fiber such as an olefin such as polyethylene or polypropylene; polyester or polyamide; a regenerated fiber such as rayon (including viscose rayon or cuprammonium rayon); or a natural fiber such as cotton can be used. A non-woven fabric obtained by an appropriate processing method such as a spun lace method, a spun bond method, a thermal bond method, a melt-blown method or a needle punching method can be used. Among these processing methods, the spun lace method is excellent in flexibility, the spun bond method is excellent in high draping properties and the thermal bond method and an air-through method are excellent in bulkiness and softness.

The absorber 4 interposed between the liquid-impermeable back sheet 2 and the liquid-permeable surface sheet 3 is formed of, for example, a fluff pulp and a super absorbent polymer. As the super absorbent polymer, a super absorbent polymer granular powder (SAP) or a super absorbent polymer fiber (SAP) can be used. Examples of the pulp include a chemical pulp obtained from lumber, cellulose fibers such as a dissolving pulp and artificial cellulose fibers such as rayon and acetate; as compared with a hardwood pulp, a softwood pulp whose fibers are long is preferably used in terms of function and price. Preferably, as a method of manufacturing the absorber 4, a fiber having thermal adhesiveness and a super absorbent polymer are mixed with a pulp, a web is formed by an air-laid method such that the thickness can be reduced and thereafter heating adhesion is performed.

The sanitary napkin 1 is effective especially when it is used as a thin slim napkin, and the thickness of the absorber at that time is preferably 0.5 to 10 mm. When the thickness of the absorber is less than 0.5 mm, an effect when an emboss 10 that will be described in detail later is provided is unlikely to be obtained, and it is more likely that the absorber is wrinkled and that side leakage occurs. On the other hand, when the thickness of the absorber is more than 10 mm, even if the emboss 10 is not provided, the absorber itself originally has sufficient rigidity, and problems such as a wrinkle in both side portions of the absorber and resulting leakage are unlikely to occur.

When the crepe paper 5 wrapping the absorber 4 is provided, as in this example, the crepe paper 5 is consequently interposed between the liquid-permeable surface sheet 3 and the absorber 4, and thus a body fluid is rapidly diffused by the crepe paper 5 excellent in absorption, and reversion of menstrual blood or the like thereof is prevented. When an air-laid absorber is used as the absorber 4, since the absorber itself has an excellent absorption performance, the crepe paper 5 does not need to be used. As the crepe paper 5, a non-woven fabric or an air-laid non-woven fabric having a low weight per unit area may be used. Without the absorber 4 being wrapped, the crepe paper 5 can be interposed only between the absorber 4 and the liquid-permeable surface sheet 3 or the crepe paper 5 can be interposed both between the absorber 4 and the liquid-permeable surface sheet 3 and between the absorber 4 and the liquid-impermeable back sheet 2.

On the other hand, in both side portions on the surface side of the sanitary napkin 1, the side non-woven fabrics 7 are provided along the longitudinal direction and substantially over the entire length of the sanitary napkin 1, and a part of the side non-woven fabrics 7 is extended laterally and wing-like flaps W are formed together with a part of the liquid-impermeable back sheet 2 likewise extended laterally.

As the side non-woven fabric 7, a water repellent processing non-woven fabric or a hydrophilic processing non-woven fabric can be used in terms of the function on which importance is placed. For example, when importance is placed on, for example, a function of preventing the penetration of a body fluid or of enhancing a feel, a water-repellent processing non-woven fabric coated with a silicon-based wafer repellent agent, a paraffin-based water repellent agent or an alkyl chromic chloride-based water repellent agent is preferably used. When importance is placed on the absorption of a body fluid in the wing-like flaps W, a hydrophilic processing non-woven fabric is preferably used in which, by a method of performing in a step of manufacturing a synthetic fiber, polymerization in the presence of a compound having a hydrophilic group (for example, an oxidation product of polyethylene glycol), or a method of performing processing with a metal salt such as stannic chloride to partially dissolve the surface to provide porosity and depositing a hydroxide of the metal, the synthetic fiber is swollen or is made porous and hydrophilicity is provided thereto by the application of capillarity.

Figure 3:
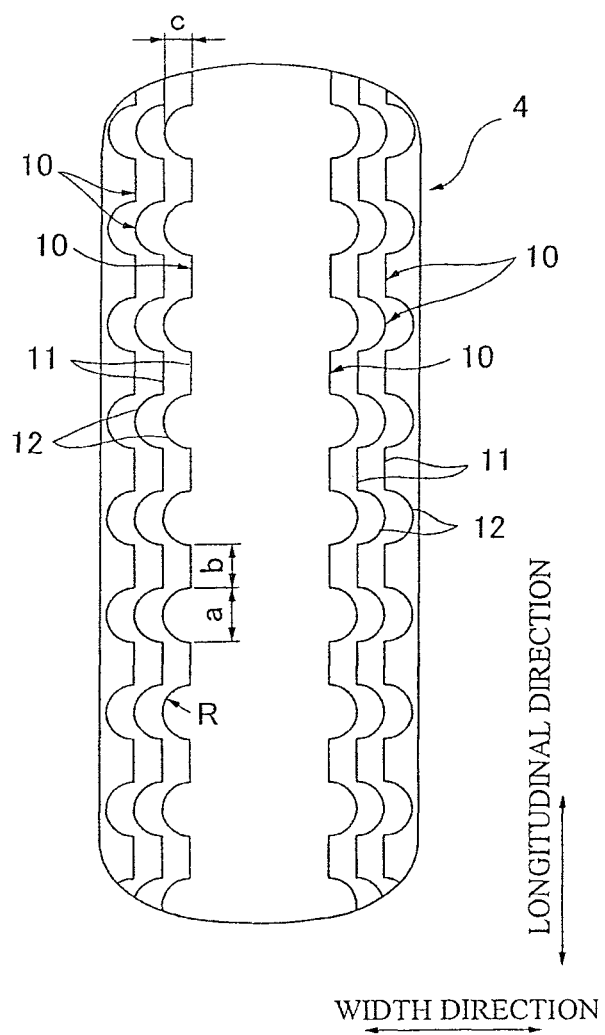
FIG. 3 is a plan view of an absorber 4.

In the sanitary napkin 1, as shown in FIG. 3, before the liquid-permeable surface sheet 3 is stacked in layers, embosses 10 are provided in both side portions of the absorber 4 substantially along the longitudinal direction, and the rigidity of the absorber 4 is increased to enhance resistance to leg pressure, with the result that the absorber 4 is unlikely to be wrinkled and that the absorbed body fluid is rapidly and effectively diffused along the direction of the grooves of the embosses 10. The emboss 10 will be described below.

[Emboss 10]

As shown in FIG. 3, the emboss 10 is formed with a plurality of straight portions 11 that are arranged a distance apart across a front end to a back end in the longitudinal direction of the absorber 4 on a straight line substantially along the longitudinal direction of the napkin; and arc-shaped portions 12 that are present between the straight portions 11 and that protrude outwardly in the direction of the width of the napkin with the end portions of the straight portion 11 being base points. The emboss 10 is formed with a pattern in which the straight portions 11 and the arc-shaped portions 12 are alternately arranged. A plurality of embosses 10, that is, one or two or more pairs of embosses 10, are arranged symmetrically in both side portions in the direction of the width of the absorber 4, and in an example shown in the figure, three embosses 10 arc-arranged a substantially equal distance apart in the direction of the width of the napkin on each of the left and right sides.

Since the embosses 10 are formed to compact both side portions of the absorber 4, and thus enhance rigidity, even if a leg pressure is applied from the outside in the direction of the width when the absorbent article is worn, the absorber 4 is unlikely to be wrinkled, and thus side leakage caused by the wrinkle can be prevented, and the diffusion of a body fluid outwardly in the direction of the width is reduced, and thus side leakage can be prevented.

Figure 4A:
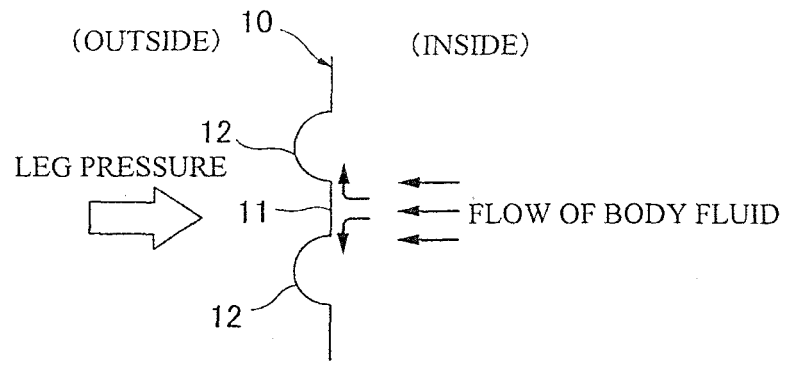
FIG. 4(A) is a schematic view showing the sanitary napkin 1 of the present invention with arrows showing the direction of leg pressure and of body fluid flow.
Figure 4B:
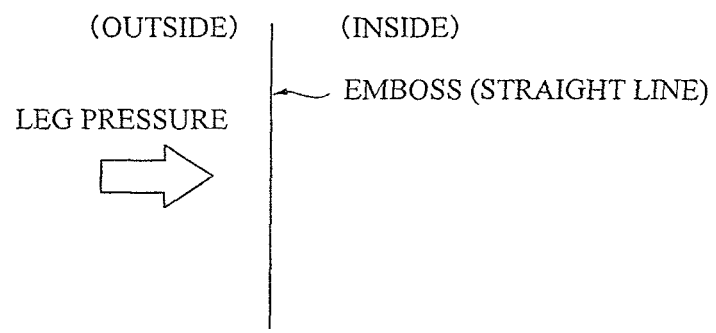
FIG. 4(B) is a schematic view showing a comparative example with an arrow showing the direction of leg pressure.

Here, a pattern in which, as shown in FIG. 4(B), a linear emboss along the longitudinal direction of the napkin is provided in order to enhance the rigidity of the absorber 4 can be considered. However, in the case of the linear embosses, due to the leg pressure from the outside in the width direction, the emboss line is more likely to be curved or bent inwardly in the width direction and resistance to the leg pressure is hardly obtained, with the result that it is impossible to reduce the occurrence of a wrinkle in the absorber. By contrast, in the sanitary napkin 1 as shown in FIG. 4(A), in particular, since the emboss 10 includes a plurality of arc-shaped portions 12 protruding outwardly in the width direction with the straight portions 11 being base points, the leg pressure from the outside in the width direction is diffused and absorbed by the arc-shaped portions 12 and can be securely received by the arc-shaped portions 12, with the result that even if the leg pressure is applied, the absorber 4 is unlikely to be wrinkled and that side leakage caused by a wrinkle can be prevented.

Since the straight portion 11 is provided between the arc-shaped portions 12, and thus the flow of the body fluid from the center portion, in the direction of the width of the absorber 4 toward the outside can be easily converted into a flow in a direction along the straight portion 11, that is, a flow in a direction along the longitudinal direction of the napkin, the diffusion toward the outside in the width direction is reduced, with the result that side leakage can be reliably prevented.

As shown in FIG. 3, the emboss 10 is preferably formed such that a dimension a of the arc-shaped portion 12 in the longitudinal direction of the napkin is longer than a dimension b of the straight portion 11 in the longitudinal direction of the napkin. As described above, since the arc-shaped portion 12 is a portion that produces resistance to the leg pressure, the dimension of the arc-shaped portion 12 is made greater than that of the straight portion 11, and thus the resistance to the leg pressure is enhanced. The dimension a of the arc-shaped portions 12 in the longitudinal direction is set equal to or more than 16 mm but equal to or less than 100 mm, and is preferably set equal to or more than 20 mm but equal to or less than 30 mm. The dimension b of the straight portion 11 in the longitudinal direction is set equal to or more than 3 mm but equal to or less than 20 mm, and is preferably set equal to or more than 5 mm but equal to or less than 10 mm.

Furthermore, the amount of protrusion c of the arc-shaped portion 12 outwardly in the direction of the width of the napkin with the straight portions 11 being the base points is set equal to or more than 3 mm but equal to or less than 10 mm, and is preferably set equal to or more than 5 mm but equal to or less than 10 mm. The arc-shaped portion 12 is preferably formed with an arc having a single radius of curvature R, and the radius of curvature R here is set equal to or more than 8 mm but equal to or less than 50 mm, and is preferably set equal to or more than 10 mm but equal to or less than 20 mm.

The width of the groove of the emboss 10 at the bottom portion of the emboss is set equal to or more than 0.5 mm but equal to or less than 3 mm, and is preferably set equal to or more than 1 mm but equal to or less than 2 mm. However, as will be described in detail later, the width of the groove of the emboss 10 may be different for each emboss line or may be partially different in one emboss line. Even in such a case, the width of the groove is preferably formed to fall within the ranges described above.

One emboss 10 is provided in each of the both side portions in the direction of the width of the absorber 4 or a plurality of embosses 10 are provided a predetermined distance apart in the direction of the width of the napkin, and preferably, a plurality of embosses 10 are provided so as to enhance resistance to a body pressure and the diffusivity of the body fluid in the longitudinal direction of the napkin. Preferably, when a plurality of embosses 10 are provided in both side portions, in all the embosses 10, the straight portions 11 and the arc-shaped portions 12 are arranged in the longitudinal direction of the napkin with the same pitch, and the straight portions 11 and the arc-shaped portions 12 are arranged such that they coincide with each other in the direction of the width of the napkin. In this way, since the arc-shaped portions 12 are formed in the direction of the width of the napkin in a multistage manner, it is possible to enhance the resistance to the leg pressure from the outside in the width direction, and moreover, since the straight portions 11 are also formed in the direction of the width of the napkin in a multistage manner, it is possible to reliably convert the flow of the body fluid from flow in the width direction toward the sides of the napkin (absorbent article) into the flow in the longitudinal direction of the napkin.

Figure 5:
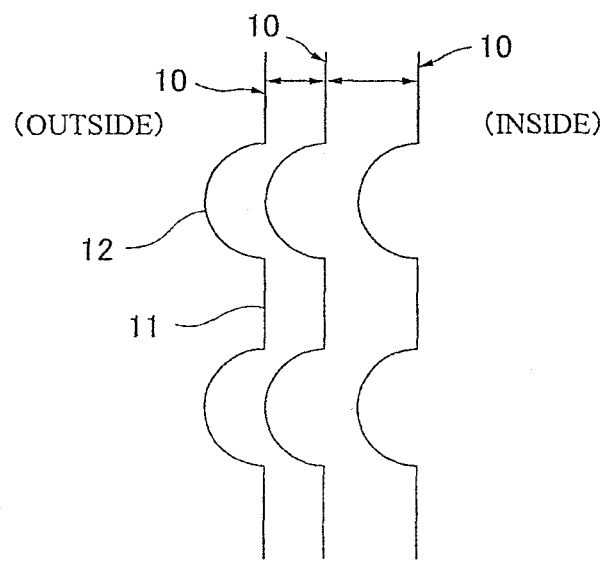
FIG. 5 is an enlarged view (No. 1) of an emboss 10.
Figure 6:
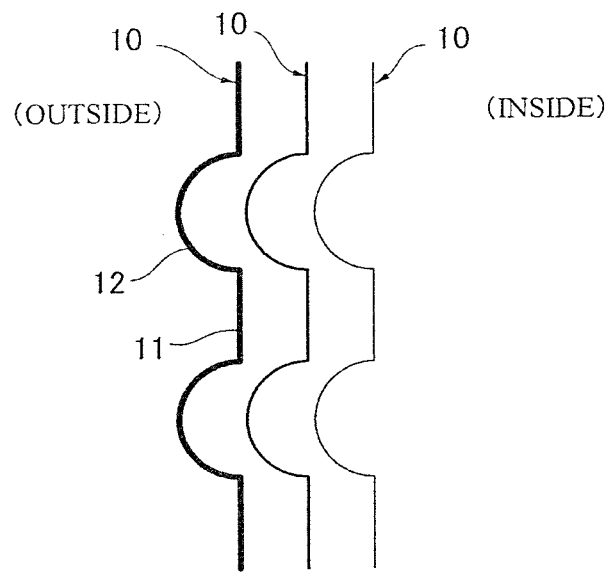
FIG. 6 is an enlarged view (No. 2) of the emboss 10.

When a plurality of embosses 10 are formed in each of the both side portions of the absorber 4, the following configurations can be adopted so that in particular, the absorber 4 on the outside in the width direction, is prevented from being wrinkled and the flow of the body fluid is easily converted on the outside in the width direction. The first one is the configuration in which, as shown in FIG. 5, the distance between the embosses 10 adjacent in the direction, of the width of the napkin and located on the outside in the width direction is narrower than the distance between the embosses 10 adjacent in the direction of the width of the napkin and located on the inside in the width direction. The second one is the configuration in which, as shown in FIG. 6, the width of the groove of the emboss 10 located on the outside in the width direction is greater than the width of the groove of the emboss 10 located on the inside in the width direction. Only one of the two configurations described above can be adopted or both thereof can be adopted at the same time. Since the region on the outside in the width direction is a region on which the leg pressure significantly acts and which is directly connected with leakage when the body fluid is diffused more outwardly, the embosses 10 in which the configurations described above are adopted are provided in the region on the outside in the width direction, with the result that the effects by the embosses 10 are enhanced.

Figure 7:
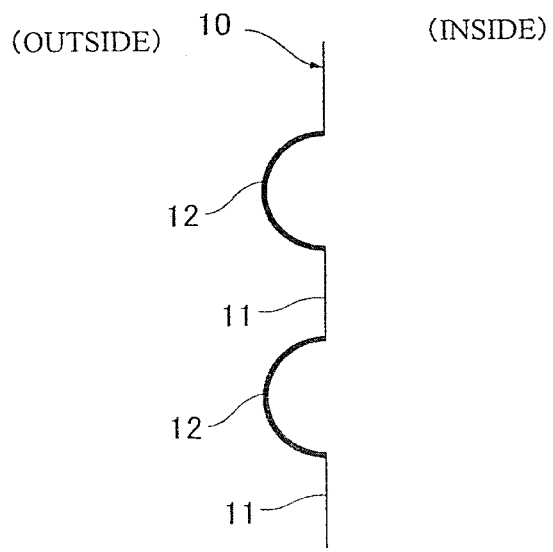
FIG. 7 is an enlarged view (No. 3) of the emboss 10.

Although the embosses 10 may be formed such that the widths of the grooves over the entire length in the longitudinal direction of the napkin are substantially equal to each other, the widths of the grooves can be partially set greater so that the resistance to the leg pressure is enhanced and that the absorber 4 is prevented from being wrinkled. Specifically, as shown in FIG. 7, over the entire length in the longitudinal direction of the napkin, or in a predetermined section in the longitudinal direction of the napkin, the width of the groove of the arc-shaped portion 12 can be set greater than the width of the groove of the straight portion 11. As described above, since the arc-shaped portion 12 is the portion that receives the leg pressure from the outside in the width direction to produce the resistance, the width of the groove of the arc-shaped portion 12 is formed to be relatively great, and thus it is possible to enhance the resistance to the leg pressure. On the other hand, as described above, the straight portion 11 is the portion that mainly plays a role in converting the flow of the body fluid that disperses from the center in the width direction toward the outside into the flow in the longitudinal direction of the napkin but is not the portion that significantly affects the resistance to the leg pressure. If the width of the groove of the straight portion 11 is increased, resistance to curving toward the longitudinal direction of the absorber 4 may occur to impair wearing comfort. Therefore, it is not desirable to increase the width of the groove of the straight portion 11.

When a plurality of embosses 10 are formed in both side portions of the absorber 4, as shown in FIG. 8, under conditions in which the adjacent embosses 10 are arranged a distance apart so as not to intersect each other, part of the arc-shaped portion 12 of the emboss 10 located on the inside in the width direction of the napkin may be arranged to enter the inside of the arc-shaped portion 12 of the emboss 10 located immediately on the outside in the width direction such that plurality of the embosses 10 are provided in the shape of multiple lines. In this way, it is possible to further enhance the rigidity of the arc-shaped portion 12, thereby increasing the resistance to the leg pressure and further reducing the wrinkling of the absorber 4. Since the straight portions 11 are also provided in the shape of multiple lines, it is possible to more reliably receive the flow of the body fluid and convert it into the flow along the straight portions 11, with the result that it is possible to reliably prevent side leakage. That the arc-shaped portion 12 on the inside in the width direction is made to enter the inside of the arc-shaped portion 12 on the outside in the width direction means that a tip end portion of the arc-shaped portion 12 on the inside in the width direction is arranged to be located on the outside in the width direction as compared with the straight portion 11 of the emboss 10 adjacent on the outside in the width direction.

Although the arc-shaped portion 12 is preferably formed with an arc having a single radius of curvature, the protrusion base end position of the arc where the arc-shaped portion 12 starts to protrude from the end portion of the straight portion 11 to the outside in the width direction can be, as shown in FIGS. 9(A), 9(B) and 9(C), arbitrarily set by a positional relationship between the maximum position IS of an imaginary circle 14 extended along the arc-shaped portion 12 in the longitudinal direction of the napkin and the straight portion 11. Specifically, the protrusion base end position may be any one of a case where as shown in FIG. 9(A), the maximum position 15 of the imaginary circle 14 in the longitudinal direction of the napkin coincides with the straight portion 11, a case where as shown in FIG. 9(B), the maximum position 15 of the imaginary circle 14 in the longitudinal direction of the napkin is present on the outside in the width direction as compared with the straight portion 11, and a case where as shown in FIG. 9(C), the maximum position 15 of the imaginary circle 14 in the longitudinal direction of the napkin is present on the inside in the width direction as compared with the straight portion 11. Since in the cases shown in FIGS. 9(A) and 9(C) the arc-shaped portion 12 is not extended from the base end portico of the straight portion 11 toward the longitudinal direction of the napkin, the rigidity of the arc-shaped portion 12 is relatively high, and the resistance to leg pressure is increased. Since in the case shown in FIG. 9(B) the arc-shaped portion 12 is extended from the base end portion of the straight portion 11 toward the longitudinal direction of the napkin, it is possible to relatively increase the length of the straight portion 11 with respect to the length of the arc-shaped portion 12, with the result that the length receiving the flow of the body fluid is increased to easily prevent side leakage.

Figure 10:
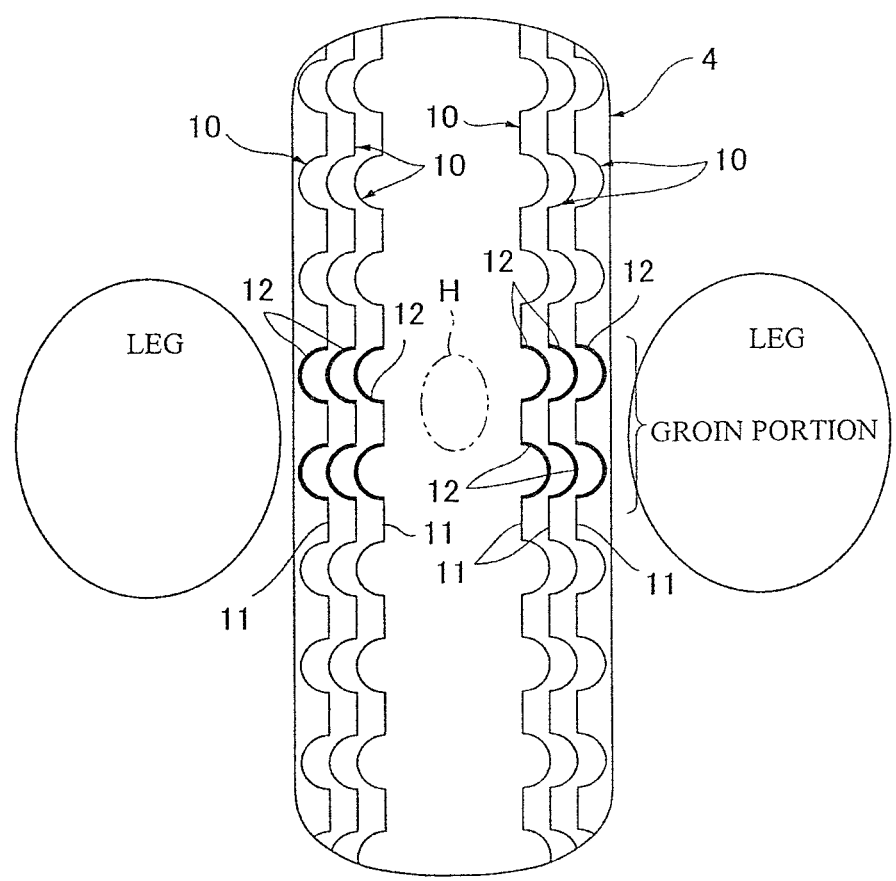
FIG. 10 is a plan view of an absorber 4 according to another embodiment.

Incidentally, when the absorbent article is worn, in a section corresponding to a groin portion, including a body fluid discharge portion H, as compared with sections in the front and back thereof the leg pressure significantly acts, and thus the embosses 10 in this section preferably have a special configuration that can cope with the leg pressure in particular. For example, the section corresponding to the groin portion when the absorbent article is worn can adopt any one of a configuration (FIG. 10) in which, as compared with the sections in the front and back thereof, the width of the groove of the arc-shaped portion 12 is set relatively great, a configuration in which the dimension a of the arc-shaped portion 12 in the longitudinal direction of the napkin is set relatively-long, a configuration in which the dimension b of the straight portion 11 in the longitudinal direction of the napkin is set relatively short, a configuration in which the radius of curvature R of the arc-shaped portion 12 is set relatively small, and a configuration in which the amount of protrusion c of the arc-shaped portion 12 outwardly in the direction of the width of the napkin with the straight portions 11 being the base points is set relatively great, or can adopt an arbitrary combination thereof.

Figure 11:
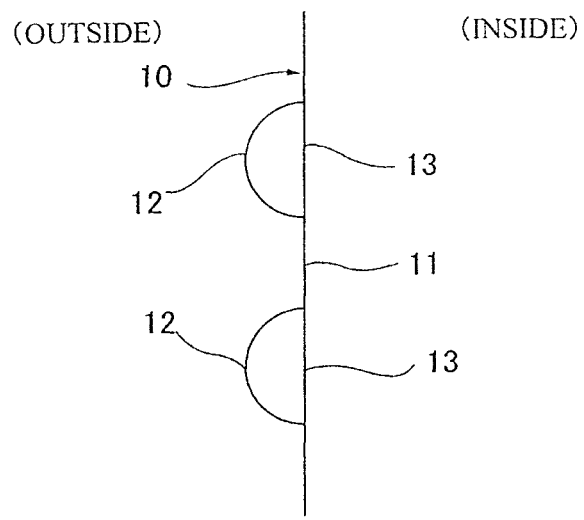
FIG. 11 is an enlarged view (No. 6) of the emboss 10.

In the emboss 10, as shown in FIG. 11, a coupling portion 13 that connects the ends of the adjacent straight portions 11 with a linear emboss is formed, and thus the straight portions 11 and the coupling portions 13 can be provided on one continuous line. In this way, the body fluid diffused from the center in the width direction toward the outside makes contact with the straight portions 11 or the coupling portions 13 without fail, and thus the flow along the straight portions 11 and the coupling portions 13 in the longitudinal direction of the napkin is easily produced, with the result that it is possible to more reliably prevent side leakage.

Figure 12:
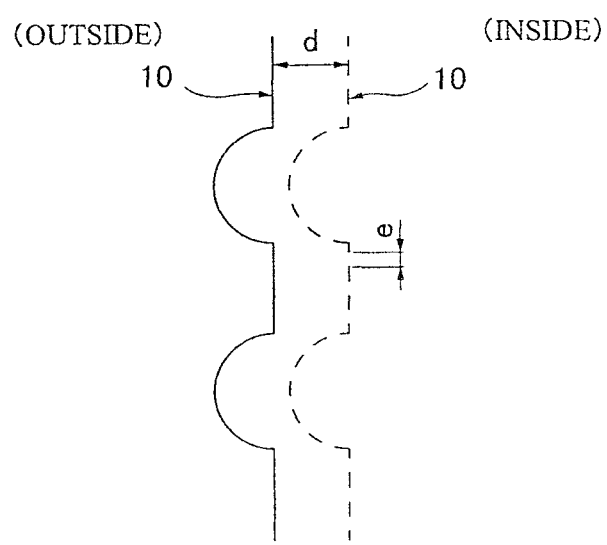
FIG. 12 is an enlarged view (No. 7) of the emboss 10.

The embosses 10 can be formed with a continuous emboss in which an emboss groove is continuous along the direction of the groove or can be formed with an intermittent emboss in which squeeze portions and intermittent portions are alternately arranged. When a plurality of embosses 10 are formed in each of both side portions of the absorber 4, all the embosses 10 can be provided either continuously or intermittently or as shown in FIG. 12, continuous embosses 10 and intermittent embosses 10 can be mixed. Preferably, when, in the embosses 10, the continuous line and the intermittent line are arranged, as in the example shown in the figure, the continuous embosses 10 are arranged on the outside in the width direction, and the intermittent embosses 10 are arranged on the inside in the width direction. In this way, the resistance to the leg pressure from the outside in the width direction is increased, and thus it is possible to reduce the wrinkling of the absorber 4, and the body fluid is more reliably received on the outside in the width direction, and thus the flow along the straight portion 11 can be produced, with the result that it is possible to reliably prevent side leakage. When the embosses 10 are provided intermittently, the intermittent length e along the direction of the emboss line is preferably set shorter than the distance d between the adjacent embosses 10 (d>e). In this way, the body fluid is more likely to flow along the intermittent embosses 10 and is unlikely to be diffused to the adjacent embosses 10.

Figure 13A:
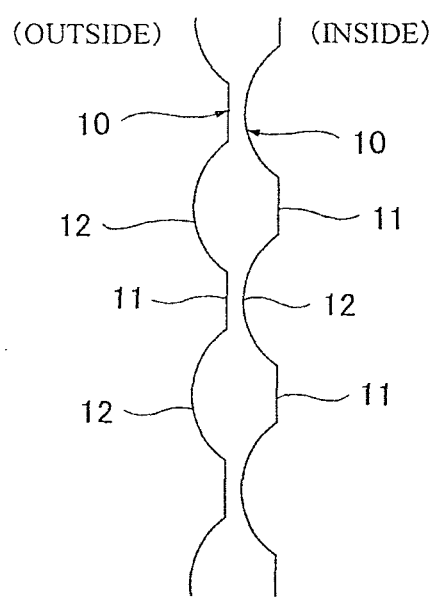
FIGS. 13(A) and 13(B) are enlarged views (No. 8) of the emboss 10.
Figure 13B:
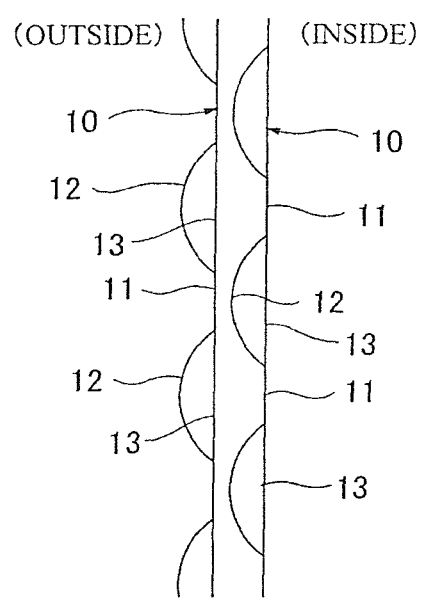

In the example of the embodiment described above, when a plurality of embosses 10 are formed in each of both side portions of the absorber 4, the arc-shaped portions 12 of the adjacent embosses 10 are arranged, in the same phases, to coincide in the width direction. However, as shown in FIG. 13, the arc-shaped portions 12 of the adjacent embosses 10 may be arranged to be out of phase in the widthwise direction of the napkin. In this way, since the arc-shaped portions 12 are present over a wider range in the longitudinal direction of the napkin, the leg pressure is reliably resisted and the absorber 4 is prevented from being wrinkled. The examples shown in FIGS. 13(A) and 13(B) are patterns in which the positions where the arc-shaped portions 12 of the adjacent embosses 10 are arranged are displaced by a half cycle, and FIG. 13(A) shows a pattern consisting of the straight portions 11 and the arc-shaped portions 12, and FIG. 13(B) shows a pattern obtained by further providing the coupling portions 13. In this way, the arc-shaped portions 12 are present over the entire length of the napkin.

In the manufacturing of the sanitary napkin 1, after the absorber 4 is wrapped with the crepe paper 5, the embosses 10 can be provided by compressing from the surface side (the surface in contact with skin, i.e., the side where the liquid-permeable surface sheet 3 is provided). When a hydrophilic second sheet (not shown) is arranged between the absorber 4 and the liquid-permeable surface sheet 3, with the absorber 4 and the second sheet stacked in layers, the embosses 10 may be provided from the surface side of the second sheet.

The invention claimed is:

1. A personal hygiene product which is a sanitary napkin, a panty liner, an incontinence pad, a medical pad or other personal hygiene item, comprising
    an absorber interposed between a liquid-permeable surface sheet and a back sheet and an emboss provided in each of both side portions of the absorber along a substantially longitudinal direction of the absorbent article,
    wherein the personal hygiene product is configured to be worn with the absorber situated between the legs of a wearer so that side portions of the absorber are subjected to pressure by the legs of the wearer,
    wherein the emboss is coplanar with a surface of the absorber and consists of a plurality of straight portions that are arranged a distance apart across a front end to a back end in the longitudinal direction of the absorber on a straight line along the longitudinal direction of the personal hygiene product and arc-shaped portions which are present between the straight portions and protrude outwardly in a direction of a width of the personal hygiene product with ends of the straight portions being base points, and the emboss is formed with a pattern in which the plurality of straight portions and arc-shaped portions are alternately arranged.

2. The personal hygiene product according to claim 1, wherein in the emboss, the base point to base point linear dimension of the arc-shaped portion in a longitudinal direction of the personal hygiene product is longer than the straight portion in the longitudinal direction of the personal hygiene product.

3. The personal hygiene product according to claim 1, wherein a plurality of the embosses are formed in each of both the side portions of the absorber, and
    in the embosses located outwardly in the width direction, as compared with the embosses located inwardly in the width direction, a distance between the adjacent embosses is narrower and/or a width of a groove of the emboss is greater.

4. The personal hygiene product according to claim 1, wherein in the emboss, width of the groove of the arc-shaped portion is greater than width of a groove of the straight portion.

5. The personal hygiene product according to claim 1, wherein a plurality of the embosses are formed in each of both the side portions of the absorber, and
    wherein adjacent said embosses are arranged a distance apart so as not to intersect each other and part of the arc-shaped portion of the emboss located inwardly in the width direction is arranged so as to enter an inside of the arc-shaped portion of the emboss located outwardly in the width direction.

6. The personal hygiene product according to claim 1, wherein a section corresponding to a groin portion of the personal hygiene product when worn has any one of a configuration in which, as compared with sections in a front and back thereof, the width of the groove of the arc-shaped portion is greater; a configuration in which the linear dimension of the arc-shaped portion in the longitudinal direction of the personal hygiene product is longer; a configuration in which the dimension of the straight portion in the longitudinal direction of the personal hygiene product is shorter, a configuration in which a radius of curvature of the arc-shaped portion is smaller, and a configuration in which an amount of protrusion of the arc-shaped portion outwardly in the direction of the width of the personal hygiene product with the straight portions being the base points is greater; or has an arbitrary combination thereof.

7. The personal hygiene product according to claim 1, wherein a plurality of the embosses are formed in each of both the side portions of the absorber, and
   wherein the arc-shaped portions of adjacent embosses in the direction of the width of the personal hygiene product are out of phase.

\* \* \* \* \*